United States Patent [19]

Schmoegner et al.

[11] Patent Number: 5,368,821
[45] Date of Patent: Nov. 29, 1994

[54] SEALABLE STERILIZER CASSETTE

[75] Inventors: John C. Schmoegner, Redondo Beach; Charles B. Swenson, Palo Verdes Pen., both of Calif.

[73] Assignee: MDT Corporation, Torrance, Calif.

[21] Appl. No.: 502,163

[22] Filed: Mar. 28, 1990

[51] Int. Cl.$^5$ .................................................. A61L 2/00
[52] U.S. Cl. ........................................ 422/116; 422/26; 422/40; 422/102
[58] Field of Search ................ 206/439, 438, 524.4; 422/26, 40, 41, 116, 297, 102; 220/87.1

[56] References Cited

U.S. PATENT DOCUMENTS

| | | |
|---|---|---|
| 4,050,894 | 9/1977 | Genis . |
| 4,105,407 | 8/1978 | Sanderson . |
| 4,149,650 | 4/1979 | Whelchel et al. . |
| 4,158,040 | 6/1979 | Miraldi ............................ 422/297 |
| 4,196,166 | 4/1980 | Sanderson et al. . |
| 4,228,914 | 10/1980 | Sanderson . |
| 4,247,517 | 1/1981 | Sanderson et al. . |
| 4,251,482 | 2/1981 | Sanderson et al. . |
| 4,349,118 | 9/1982 | Sanderson et al. . |
| 4,372,921 | 2/1983 | Sanderson et al. . |
| 4,374,570 | 2/1983 | Sanderson et al. . |
| 4,416,417 | 11/1983 | Sanderson et al. . |
| 4,551,311 | 11/1985 | Lorenz .............................. 422/26 |
| 4,558,632 | 12/1985 | Sanderson et al. . |
| 4,584,182 | 4/1986 | Sanderson et al. . |
| 4,612,872 | 9/1986 | Whelchel et al. . |
| 4,748,003 | 5/1988 | Riley ................................ 422/26 |
| 4,759,909 | 7/1988 | Joslyn ............................... 422/26 |
| 4,781,898 | 11/1988 | Jones ................................ 422/26 |
| 4,915,606 | 4/1990 | Shimokawa ....................... 422/295 |
| 4,971,764 | 11/1990 | Albright ........................... 422/113 |

FOREIGN PATENT DOCUMENTS 7900077 2/1979 WIPO ............................ 220/87.1

Primary Examiner—Lyle A. Alexander
Attorney, Agent, or Firm—Trask, Britt & Rossa

[57] ABSTRACT

A sterilizing cassette system is disclosed. A sealed container (cassette) is provided and configured to receive an article to be sterilized (i.e. a load). A sealing member, such as a plunger, is associated with the cassette at an opening formed in the cassette. An actuating member, such as a motor, is mechanically associated with the sealing member to open and close the sealing member at preselected times during the sterilizing cycle. A control device, such as a microprocessor, is associated with the actuating member to provide signals to the actuator to cause it to actuate the plunger at preselected times in the sterilizing cycle. The actuator is formed integral with the sterilizer so that it can be interchangeably used with multiple load-bearing cassettes. Once the cassette is removed from the sterilizer, it remains in its sealed state until the load is needed, thus mainlining the load in a sterilized condition.

13 Claims, 1 Drawing Sheet

SEALABLE STERILIZER CASSETTE

BACKGROUND OF THE INVENTION

1. Field

The present invention is directed to a cassette system having a removable container to be used with a sterilizer. A sealable opening member is associated with the container and operated by an actuating unit and a control circuit during the sterilizing cycle.

2. State of the Art

After medical and dental instruments and other devices are sterilized, they are often stored for a period of time before they are used. After such devices are removed from a sterilizer, they can be easily contaminated. Therefore, some means of protecting the device after sterilization is advantageous.

One method for preserving sterility is to wrap the surgical instrument or other item in towels which are then enclosed in a sheet and taped to create a "wrapped load." During sterilization, however, the wrapping may tend to prohibit complete penetration of the sterilizing steam or gas. Additionally, the wrapping may inhibit complete removal of moisture from the load during a drying phase. Such wrapped loads may also have a limited shelf life, since ambient air may penetrate the wrap.

Certain containers have been devised which remain in an open configuration within a sterilizer (to allow sterilization of devices held within the container), but which close prior to the door of the sterilizer being opened. These containers utilize various meltable fuses or mechanical mechanisms that react to temperature or pressure conditions to seal the load within the container at a particular point in the sterilizing cycle.

For example, U.S. Pat. Nos. 4,251,482 (Sanderson et al.), 4,247,517 (Sanderson et al.), and 4,228,914 (Sanderson), disclose containers with a pressure-responsive valve in a bottom wall. The valve allows steam to circulate within the container while the load is sterilized but then closes in response to conditions in the sterilizer during a vacuum phase. U.S. Pat. Nos. 4,584,182 (Sanderson et al.), 4,558,632 (Sanderson et al.), 4,374,570 (Sanderson et al.), 4,372,921 (Sanderson et al.), and 4,416,417 (Sanderson et al.) disclose containers with a lid held open by a pressure-responsive support mechanism. Some portion of the support mechanism reacts to conditions in the sterilizer to drop the lid onto a lower base portion.

U.S. Pat. Nos. 4,612,872 (Whelchel et al.), 4,349,118 (Sanderson et al.), 4,196,166 (Sanderson et al.) and 4,149,650 (Whelchel et al.) disclose containers in which a closing device has a "fuse" formed of a substance that melts when subjected to certain temperature and pressure conditions. When the fuse melts, the valve shuts thereby to seal the container. U.S. Pat. No. 4,105,407 (Sanderson) discloses a system in which a piston responds to pressure conditions within the sterilizer. The piston acts against a camming device thereby to seal and close the container. The container is closed by means of a sliding lid structure. U.S. Pat. No. 4,050,894 (Genis) discloses a normally solid petroleum product associated with a load-holding capsule. In response to conditions in the sterilizer, the petroleum product liquefies to surround and cover the capsule. The petroleum product subsequently resolidifies to hermetically seal the capsule.

Because such systems respond to temperature and pressure conditions in the sterilizer to actuate the closing or sealing device, they may not be precisely controllable. In addition, once the sealing has taken place, it may not be possible for the container to open itself again for additional sterilizing procedures.

There remains a need for a sterilizer cassette system to effect a sealing of the container at desired times in the sterilizing cycle.

SUMMARY OF THE INVENTION

The present invention provides a cassette system to be used with a sterilizer during a sterilizer cycle. A container is provided adapted to receive an article to be sterilized. The container is configured for placement in a sterilizer during the sterilizing cycle. A sealing member is movably associated with the container to operate between a first position to seal the interior of the container from the environment, and a second position to permit gaseous interchange between the interior of the container and the environment. Actuation means is mechanically associated with the sealing member to operate the sealing member between its first and second positions. A control device is operatively linked with the actuation means and is adapted to provide signals to the actuation means at preselected times during the sterilizing cycle. The signals effect operation of the sealing member between its first and second positions.

The sealing member may be a plunger slidingly mounted to the container to associate with an opening formed in the container. The actuation means may be formed integral with the sterilizer, the activation means being adapted to mechanically disengage from the sealing member when the container is removed from the sterilizer. The control device may include computation means programmed to provide the signals to the actuation means at the preselected times.

In one preferred embodiment, the actuation means is a motor. The motor may be linked with the sealing member, e.g. a plunger, by means of a rack and pinion gearing relationship. The pinion gear may be attached to the shaft of the motor, with the plunger carrying a rack gear. The plunger is moved between its first and second positions by means of the pinion gear rotating to urge the plunger towards its first or second positions. In such an arrangement, the plunger is preferably associated with a biasing means, such as a spring, to urge the plunger towards its second or sealed position. The plunger thus remains in this sealed position when the container is removed from the sterilizer.

Sterilizing cassette systems of the invention allow for loads held in the container to be subjected to various phases of the sterilizing cycle, but allow for the container to be sealed prior to removal from the sterilizer. The container can then be stored with its load until the medical instrument or other device is needed. Such cassette systems allow for the sealing of the container to occur at a preselected time when a positive signal is delivered from the control device to the actuation means, thus removing the possibility of error. Several containers may be fashioned to cooperate with a single actuation means.

BRIEF DESCRIPTION OF THE DRAWINGS

In the drawings, which illustrate that which is presently regarded as the preferred embodiment of the invention.

DETAILED DESCRIPTION OF THE ILLUSTRATED EMBODIMENT

Figure 1:
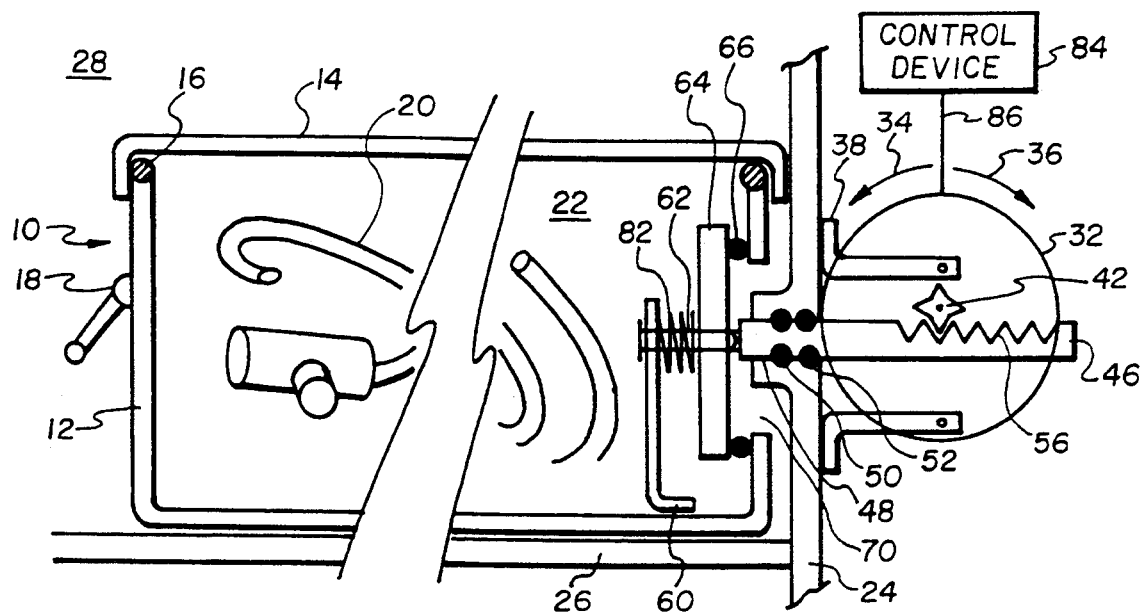
FIG. 1 is a schematic sectional view of a cassette system of the invention with the sealing member in its first or sealed position.

Referring to FIG. 1, a cassette or container generally indicated at 10 includes a tray 12 and an associating lid 14. A rubber-like seal 16 is formed around the upper edge of tray 12 as shown. Lid 14 sealingly associates with gasket 16. A locking mechanism 18, shown schematically, is adapted to tray 12 to lock lid 14 in place as shown in FIG. 1 to create an air-tight seal between lid 14 and tray 12. The container formed by the association of tray 12 and lid 14 may be formed in any convenient shape, such as, for example, a cylindrical or rectangular box. A load 20, which is intended to depict a typical endoscope, is placed within container 10 before lid 14 is placed on tray 12.

Figure 2:
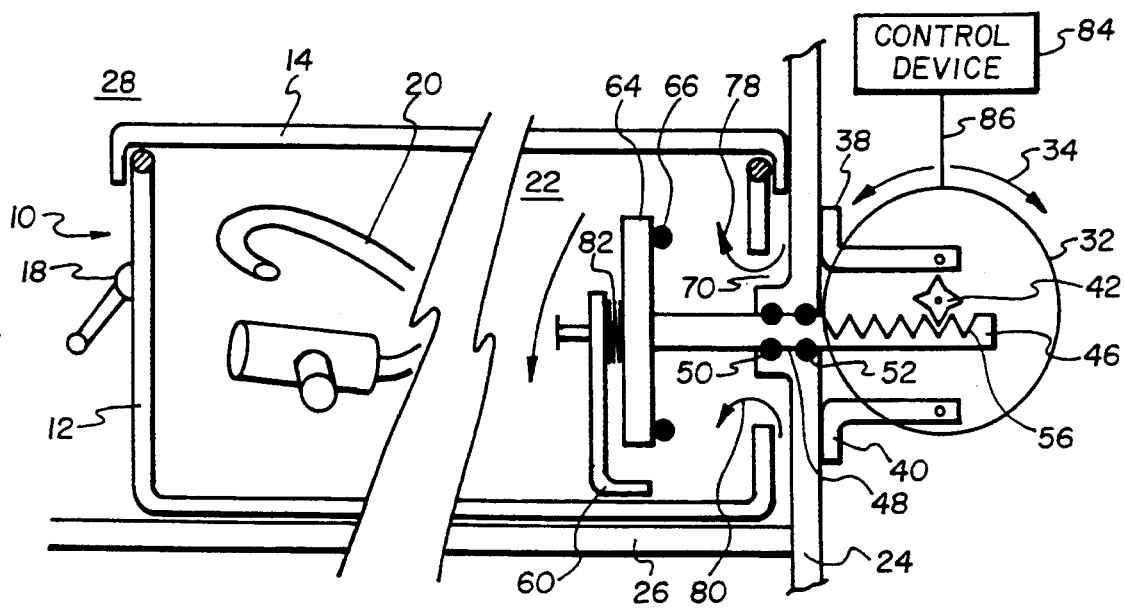
FIG. 2 is a schematic partial sectional view of the sterilizer cassette system of FIG. 1 with the sealing member in its second or open position.

Cassette or container 10 is shown in FIGS. 1 and 2 in place within a sterilizer having a wall portion 24. Container 10 resides upon a shelf guide 26 and is held firmly in place by an appropriate bracket or mounting. Container 10 is placed to be within the interior 28 of the sterilizer.

Mounted to the sterilizer is a motor 32 adapted to rotate in either direction 34 or 36. Motor 32 is attached to brackets 38 and 40. Mounted to the rotating shaft of motor 32 is a pinion gear 42. A shaft 46 is mounted to slidingly associate with sterilizer wall 24 at an opening 48 formed to have the same internal dimension and cross-section as the exterior of shaft 46. A pair of rubber-like seals 50 and 52 are positioned in opening 48 to provide an air-tight seal between sterilizer wall 24 and shaft 46.

Shaft 46 contains a number of rack gears 56, as shown, which associate with pinion gear 42. As pinion gear 42 rotates in either direction 34 or 36, it associates with gears 56 to urge shaft 46 between its positions shown in FIGS. 1 and 2.

A bracket 60 is mounted to the interior of tray 12, as shown. Attached to bracket 60 is a shaft 62. Shaft 62 slidingly associates with bracket 60. A plunger 64 is attached to shaft 62 to move with shaft 62 between a first and second position as shown respectively in FIGS. 1 and 2. A rubber-like seal 66 is attached to plunger 64.

Figure 3:
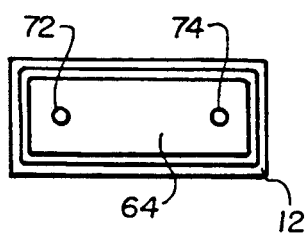
FIG. 3 is an end view of a plunger assembly of the invention.
Figure 4:
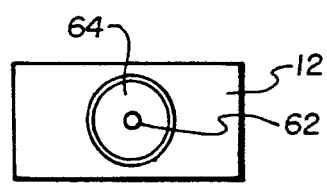
FIG. 4 is an end view of an alternative embodiment of a plunger assembly of the invention.

An opening 70 is formed in tray 12. Opening 70 is configured to have the same cross-sectional shape as plunger 64, plunger 64 being larger, however, in cross-sectional dimension. FIGS. 3 and 4 depict alternative configurations for the cross-sectional shapes of plunger 64. In FIG. 3, plunger 64 has a rectangular cross-section and attached to two shafts 72 and 74, which are cylindrical and are adapted to perform the same function as shaft 62. In the embodiment of FIG. 3, the opening similar to opening 70 would also be rectangular in cross-section. In FIG. 4, plunger 64 is formed to have a circular cross-section and attached to a single cylindrical shaft 62.

In the configuration shown in FIG. 1, plunger 64 and seal 66 associate with tray 12 at opening 70 to seal the interior 22 of container 10 from its external environment, i.e., the environment found in the interior 28 of the sterilizer. Motor 32 may be rotated clockwise as shown in FIGS. 1 and 2 or in the direction of arrow 36, to urge plunger 64 and seal 66 away from the interior of tray 12 to allow gases in the interior 28 of the sterilizer to enter the interior 22 of container 10, as indicated by arrows 78 and 80. In this configuration, gases may also be drawn from the interior 22 of container 10 by means of a vacuum or negative pressure being created within the interior 28 of the sterilizer.

At any point in the sterilizing cycle, and particularly at the end of the cycle, plunger 64 may be returned to its position shown in FIG. 1 to seal the interior 22 of container 10 from the environment to thereby protect the sterility of load 20 until it is necessary to use load 20. A spring 82 is positioned on shaft 62 between bracket 60 and plunger 64 to urge plunger 64 away from bracket 60 and toward its position shown in FIG. 1. Thus, spring 82 acts to maintain plunger 64 in its sealed position, for example, when load 20 is stored outside the sterilizer.

A control device 84 is electronically linked by means of control lines 86 to motor 32. Control device 84 may be, for example, a microprocessor associated with an appropriate relay device and programmed to actuate motor 32 to urge plunger 64 in either its position shown in FIG. 1 or FIG. 2. This microprocessor or control device may also be used to control sterilizing activities of the sterilizer. In the illustrated embodiment, the control device and motor are formed integral with the sterilizer. Depending upon the sterilization cycle, the control device may be programmed to open and close opening 70 in tray 12 at various times or during various phases of the sterilizing cycle.

Shaft 46 with its gears 56 and pinion gear 42 are adapted to disengage from each other when container 10 is removed from the sterilizer. When container 10 is removed from the sterilizer, shaft 46 remains in place and integral with the sterilizer, preferably in its position shown in FIG. 1 to be in place ready to receive another container with a load to be sterilized.

In use, with the container 10 out of the sterilizer, lid 14 is removed from tray 12 by appropriately manipulating locking mechanism 18. If an instrument such as load 20 is sterilized and within the interior 22 of container 10, it is removed and utilized immediately, or as soon as possible.

When it is time again to use container 10 for a further sterilization, a load is placed within the interior 22 and lid 14 replaced. Lid 14 is firmly sealed on tray 12 by locking mechanism 18. The container is placed within the sterilizer in its position shown in FIG. 1 and firmly locked in place. The door to the sterilizer is closed, and the appropriate controls are set to begin the sterilizing cycle. During the sterilizing cycle, at appropriate times, motor 32 rotates to urge plunger 64 to its position shown in FIG. 2. The position shown in FIG. 1 is a first or sealed position, and the position shown in FIG. 2 is a second or opened position.

Before the door to the sterilizer is opened, the control device 84 is programmed to return plunger 64 to its position shown in FIG. 1 to thereby seal the interior 22 of the container. Container 10 may be then removed from the sterilizer as before described.

Reference herein to details of the illustrated embodiment is not intended to limit the scope of the appended claims, which themselves recite those features regarded as important to the invention.

What is claimed:

1. A sterilization cassette system, comprising:
   a container adapted to receive an article to be sterilized and configured for placement in the sterilizing chamber of a sterilizer;
   a sealing member movably associated with said container to operate between a first position which seals the interior of said container from the environment external said container and a second position which permits gaseous interchange between said interior and said external environment;
   actuation means mechanically associated with said sealing member to operate said sealing member between said first and second positions; and
   a control device operatively linked with said actuation means and adapted to provide actuation signals to said actuation means at preselected times during said sterilizing cycle, thereby to cause said actuation means to operate said sealing member between said first and second positions.

2. A cassette system according to claim 1 wherein said sealing member comprises a plunger slidably mounted to said container to associate with an opening formed in said container.

3. A cassette system according to claim 1 in combination with the sterilizer wherein said actuation means is formed integral with said sterilizer, and said actuation means is constructed so as to mechanically disengage from said sealing member when said container is removed from said sterilizer.

4. A cassette system according to claim 1 wherein said control device includes computation means programmed to provide said actuation signals to said actuation means at said preselected times.

5. A cassette system in combination with a sterilizer, said cassette system being adapted to be used with said sterilizer during a sterilizing cycle, comprising:
   a container constructed so as to open to receive articles to be sterilized and to close, thereby to isolate its interior from the external environment, said container being configured and adapted to be placed in said sterilizer during said sterilizing cycle and to be removed subsequent to said sterilizing cycle;
   a sealing member positioned and arranged with respect to said container so as to move between a first position, which seals the interior of said container, and a second position, which permits gaseous communication between said interior and said external environment;
   an actuator positioned and arranged with respect to said sterilizer and mechanically linked with said sealing member to urge said sealing member between its said first and second positions; and
   a control circuit linked with said actuator and positioned and arranged so as to provide actuation signals to said actuator at preselected times during said sterilizer cycle, thereby to cause said actuator to urge said sealing member between its said first and second positions.

6. A cassette system according to claim 5 wherein said sealing member comprises a plunger operatively associated with an opening formed in said container.

7. A cassette system according to claim 6 wherein said actuator is integrally formed with said sterilizer so as to disengage from said plunger upon removal of said container from said sterilizer.

8. A cassette system according to claim 7 wherein said actuator includes a rotating motor.

9. A cassette system according to claim 8 wherein said motor is mechanically associated with said plunger by means of a rack and pinion gear assembly.

10. A cassette system in combination with a sterilizer, said cassette system being adapted to be used in said sterilizer during a sterilizing cycle, comprising:
    a container constructed so as to open to permit the introduction to its interior of articles to be sterilized and to close to seal said interior, said container configured to be placed in said sterilizer during said sterilizing cycle and to be removed from said sterilizer subsequent to said sterilizing cycle;
    a plunger associated with an opening formed in said container to slide between a first position to seal said opening and a second position to permit gaseous communication through said opening between said interior and the exterior environment;
    biasing means associated with said plunger for urging said plunger toward its said first position and to hold said plunger in said first position when said container is removed from said sterilizer;
    an actuator integral with said sterilizer and positioned and arranged so as to mechanically link with said plunger when said container is placed in said sterilizer to operate said plunger between its said first and second positions and to disengage from said plunger when said container is removed from said sterilizer; and
    a control device associatively linked with said actuator to provide actuation signals to said actuator at preselected times during said sterilizing cycle to cause said actuator to operate said plunger between its said first and second positions.

11. A cassette system according to claim 10 wherein said actuator comprises a motor mechanically linked with said plunger by a pinion gear connected to said motor and a rack gear connected to said plunger.

12. A cassette system according to claim 10 wherein said control circuit includes a microprocessor programmed to provide said signals to said actuator at said preselected times.

13. A cassette system according to claim 12 wherein said actuator comprises a motor mechanically linked with said plunger by a pinion gear connected to said motor and a rack gear connected to said plunger.

* * * * *